US008887913B2

(12) United States Patent
Wood

(10) Patent No.: US 8,887,913 B2
(45) Date of Patent: Nov. 18, 2014

(54) GROMMET MATRIX

(75) Inventor: Timothy E. Wood, Weare, NH (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 1969 days.

(21) Appl. No.: 11/315,379

(22) Filed: Dec. 19, 2005

(65) Prior Publication Data

US 2007/0138042 A1 Jun. 21, 2007

(51) Int. Cl.
*B65D 83/04* (2006.01)
*A61C 3/04* (2006.01)

(52) U.S. Cl.
CPC .......................................... *A61C 3/04* (2013.01)
USPC ............................. 206/369; 206/477; 206/338

(58) Field of Classification Search
USPC .......... 206/369, 370, 477, 438, 820, 338, 340, 206/341, 336, 368, 372; 29/464, 450; 439/77, 83, 84
See application file for complete search history.

(56) References Cited

U.S. PATENT DOCUMENTS

| | | | | | |
|---|---|---|---|---|---|
| 3,097,360 | A | * | 7/1963 | Carlson, Jr. et al. | 206/346 |
| 3,624,867 | A | * | 12/1971 | Reynolds | 29/413 |
| 3,900,393 | A | * | 8/1975 | Wilson | 209/399 |
| 4,442,938 | A | * | 4/1984 | Murphy | 206/728 |
| 4,615,927 | A | * | 10/1986 | Holzmann | 206/714 |
| 4,851,964 | A | * | 7/1989 | Endo | 361/748 |
| 4,936,012 | A | * | 6/1990 | Shepherd | 29/845 |
| 4,946,386 | A | * | 8/1990 | Kidd et al. | 433/18 |
| 5,340,551 | A | | 8/1994 | Berry, Jr. | 422/300 |
| 5,397,254 | A | * | 3/1995 | Powell | 439/885 |
| 5,492,671 | A | | 2/1996 | Krafft | 422/26 |
| 5,511,661 | A | * | 4/1996 | Karlis et al. | 206/338 |
| 5,518,115 | A | * | 5/1996 | Latulippe | 206/370 |
| 5,525,314 | A | | 6/1996 | Hurson | 422/300 |
| 5,529,490 | A | * | 6/1996 | Klein et al. | 433/3 |
| 5,827,487 | A | | 10/1998 | Holmes | 422/297 |
| 6,099,812 | A | | 8/2000 | Allen et al. | 422/300 |
| D445,197 | S | | 7/2001 | Frieze et al. | D24/217 |
| 6,256,879 | B1 | * | 7/2001 | Neidich et al. | 29/843 |
| D446,018 | S | | 8/2001 | Streich et al. | D3/319 |
| 6,713,029 | B1 | | 3/2004 | Krafft et al. | 422/300 |

FOREIGN PATENT DOCUMENTS

GB          2290774 A  *  1/1996

* cited by examiner

*Primary Examiner* — Steven A. Reynolds
(74) *Attorney, Agent, or Firm* — Taylor IP, P.C.

(57) ABSTRACT

A dental case including a substrate having a plurality of holes therein and a grommet matrix. The grommet matrix including a plurality of grommets each having a groove. The plurality of grommets are interconnected outside of said groove and the plurality of grommets are located at predetermined positions corresponding to the plurality of holes.

10 Claims, 4 Drawing Sheets

GROMMET MATRIX

BACKGROUND OF THE INVENTION

1. Field of the Invention.

The present invention relates to a flexible grommet, and, more particularly, to a method of insertion of flexible grommets.

2. Description of the Related Art.

Grommets are well known and are utilized in a variety of forms. One form of grommet is a metal grommet that is applied to a fabric or leather to define a hole through which a fastening device may be inserted. For example, metal grommets are utilized to form passageways for a shoe string for a shoe. Additionally, metal grommets are used in military and outdoor equipment to provide predefined and pre-spaced patterns of holes for the insertion of connecting apparati, such as a military utility belt. Metal grommets may be pressed through the material forming an opening and then a portion of it is bent over thereby retaining the grommet in the material. Alternatively, metal grommets are sometimes formed of two parts which are joined together in a crimping operation.

Rubber or polymer grommets are widely used in electronics equipment to form a non-abrasive passageway for an electric wire a metal wall. A hole is drilled in the metal and the grommet is compressed and inserted partway through so that the groove of the grommet engages the wall of the case forming a reduce size hole that is fully cushioned by the grommet in the metal wall.

Rubberized grommets are additionally utilized in surgical cases to hold surgical instruments such as dental burs and other surgical tools. Grommets are inserted through holes in a portion of a surgical case so that the resilient nature of the grommet adds to the secure holding of the surgical or dental instrument therein.

The problem with the insertion of rubberized grommets is that it is a time consuming task and that it can result in damage or degradation of the grommet if improperly installed.

What is needed in the art is a cost effective method of inserting grommets.

SUMMARY OF THE INVENTION

The present invention consists of a grommet matrix and method of inserting a plurality of grommets nearly simultaneously.

The invention comprises, in one form thereof, a method of inserting grommets including the steps of aligning a grid of grommets with a plurality of openings in a substrate and engaging the grid of grommets with the openings in the substrate.

Another embodiment of the present invention consists of a dental case including a substrate having a plurality of holes therein and a grommet matrix. The grommet matrix includes a plurality of grommets each having a groove. The plurality of grommets are interconnected outside of the groove and are located at predetermined positions corresponding to the plurality of holes.

An advantage of the present invention is that several grommets may be inserted into a pattern of holes nearly simultaneously with one operation.

Another advantage of the present invention is that the membrane holding the grommets in predefined positions is easily removed once the grommets are inserted in their respective holes.

Yet another advantage of the present invention is that it significantly reduces the amount of time required to insert multiple grommets into respective holes.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
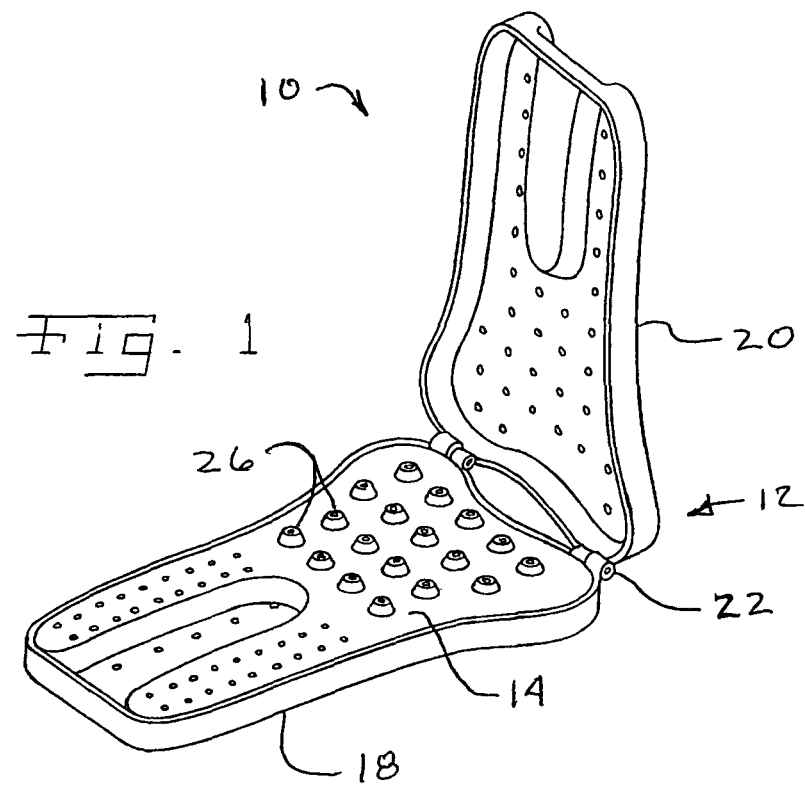
FIG. 1 illustrates one embodiment of a dental case having grommets inserted by the method of the present invention.

Referring now to the drawings, and more particularly to FIG. 1, there is illustrated a surgical case 10 including a housing 12, a substrate 14 and a grommet matrix 16 also known as a matrix grid 16.

Figure 2:
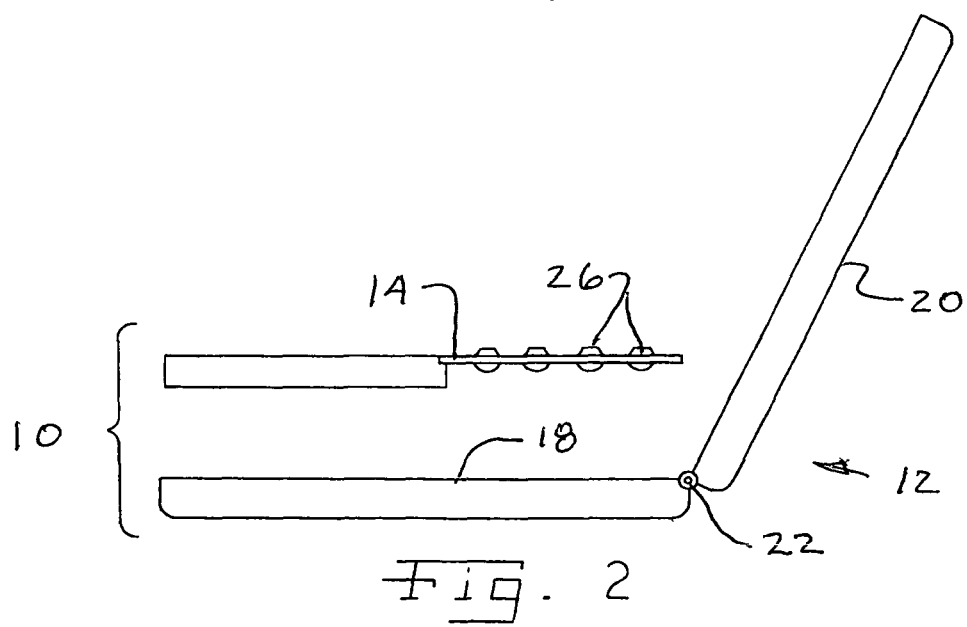
FIG. 2 illustrates an exploded view of the dental case of FIG. 1.
Figure 3:
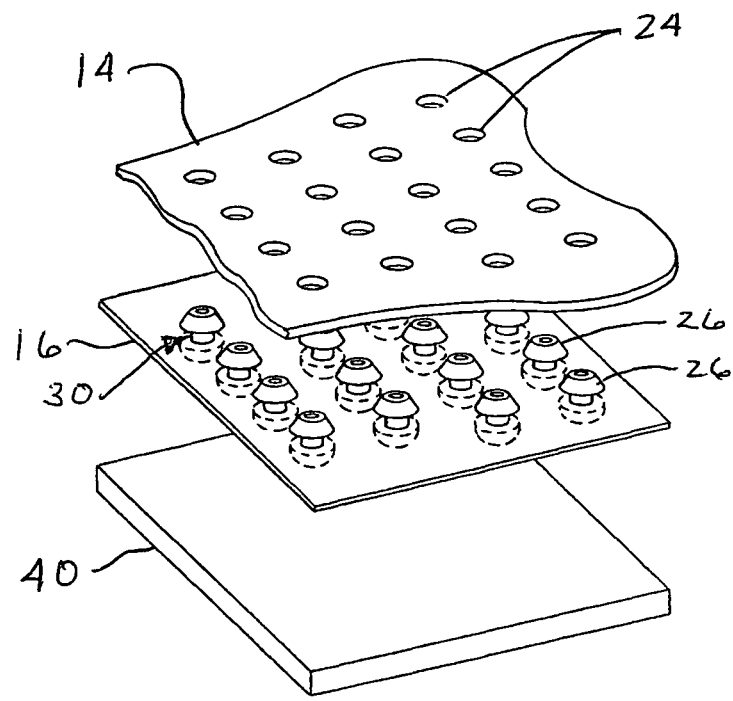
FIG. 3 illustrates a grommet matrix of the present invention used in FIGS. 1 and 2.
Figure 4:
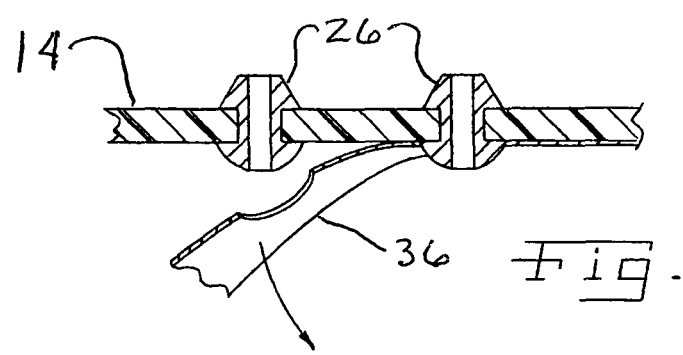
FIG. 4 illustrates removal of a portion of a membrane from the grommets once they are installed in the tray of FIGS. 1-3.
Figure 5:
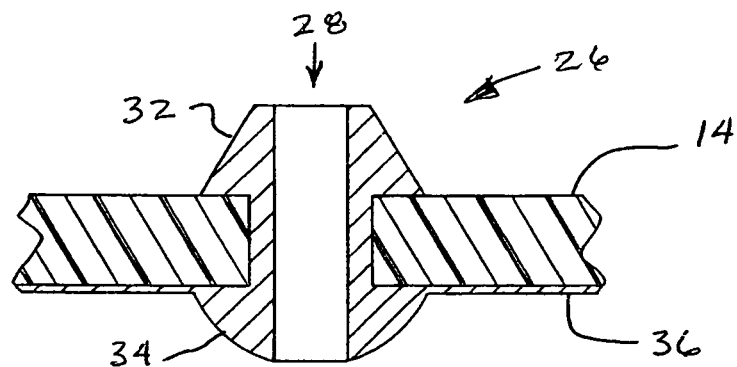
FIG. 5 shows an expanded cross-sectional view of a single grommet inserted into the tray of FIGS. 1-4.
Figure 6:
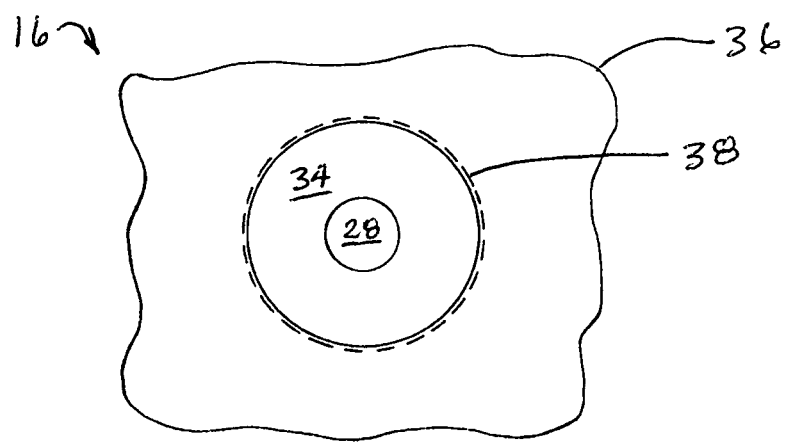
FIG. 6 is a bottom view of a portion of the grommet matrix of FIGS. 3-5.

Now, additionally referring to FIG. 2 there is illustrated housing 12 having a lower portion 18, an upper portion 20 and a hinge 22. Substrate 14, also known as a tray 14, is placed within housing 12, which may have standoffs to hold substrate 14 at an elevated position relative to the bottom of lower portion 18. Lower portion 18 and upper portion 20 are connected by way of hinge 22, that allows upper portion 20 to be rotated relative to lower portion 18 to expose the instruments, not shown, held by substrate 14 and grommet grid 16.

Now, additionally referring to FIGS. 3-6, substrate 14 has holes 24 formed therethrough in a pattern, which is defined by ergonomics and the desired placement of instruments or a holding apparatus that may be inserted through grommets 26. Although holes 24 are illustrated as being cylindrical in nature, other shapes of holes along with grommets to accommodate the shape are also contemplated. Substrate 14 is removable from housing 12 and can be secured thereto by fasteners, not shown.

Grommet grid 16 includes numerous grommets 26 that are spaced and held in a pattern that corresponds to the pattern of holes 24 in substrate 14. Each grommet 26 has a hole 28 that traverses grommet 26. Hole 28 may have ridges therein to accommodate the holding of instruments and to allow the passage of heated sterilizing vapors and/or fluids therethrough. Each grommet 26 has a groove 30 which is of sufficient depth to appropriately accommodate hole 24. A top portion of grommet 26 includes a head 32, which may have a trapezoidal cross-sectional shape. A bottom 34 of grommet 26 may be rounded or of some other shape. Although the illustrated method shows a head 32 which is inserted through an underside portion of substrate 14, it can be easily understood that head 32 may be inserted through a top portion of substrate 14 presenting bottom 34 to the user.

A membrane 36 connects grommets 26 so that grommets 26 are pre-positioned in a pattern, which corresponds to the pattern of holes 24. Membrane 36 may be made of the same material as grommets 26. Membrane 36 is formed at the same time that grommets 26 are molded. Alternatively, membrane 36 may be attached to grommets 26 in a subsequent operation. While membrane 36 may remain with grommets 26, alternatively a portion of membrane 36, proximate to grommets 26, may include a weakened line 28 or a perforation 38, which assists in the removal of membrane 36 from grommets 26 once they are inserted through holes 24 of substrate 14.

Grommet matrix 16 is positioned so as to align grommets 26 with holes 24 of substrate 14 and a pressing plate 40 causes head 32 of each of grommet 26 to engage a corresponding hole 24. As pressure is applied to pressing plate 40, head 32 proceeds through hole 24 and then extends on an opposite side of substrate 14 when it is fully installed. Pressing plate 40 along with any other holding fixture, not shown, that may assist in holding substrate 14 is removed. Membrane 36 is then pulled causing it to tear away along perforations 38 leaving grommets 26 connected only by way of their installed positions within substrate 14.

Alternatively, pressing plate 40 may be shaped to accommodate bottom 34 of grommets 26 so that it may assist in the positioning of grommet matrix 16 relative to substrate 14 in the assembly operation. Advantageously, the present invention allows for a rapid insertion of multiple grommets nearly simultaneously, thereby eliminating significant amounts of machine time or manpower for the insertion of single grommets in a sequential manner.

Figure 7:
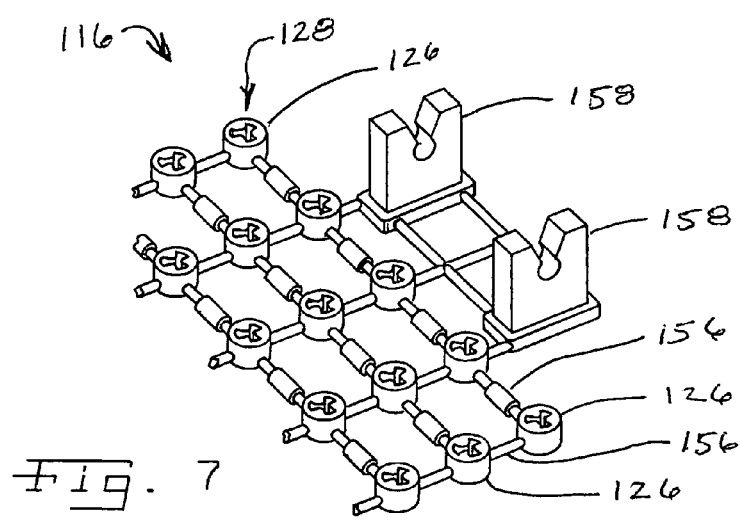
FIG. 7 is a perspective view of another embodiment of a grommet matrix of the present invention.
Figure 8:
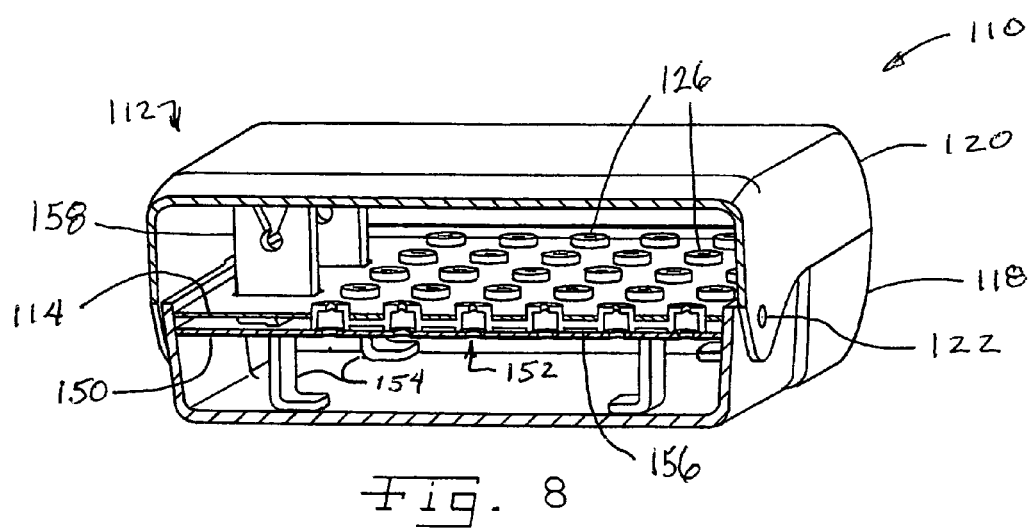
FIG. 8 is a partially sectioned perspective view of another embodiment of a dental case using the grommet matrix of FIG. 7.

Now, additionally referring to FIGS. 7 and 8, there is shown another embodiment of a surgical case 110 that is similar to surgical case 10 having similar features thereto and with numbers being advanced by 100. Housing 112 has a lower portion 118, an upper portion 120 and a hinge 122. A substrate 114, also known as a tray 114, has a grommet matrix 116 associated therewith such that grommets 126 extend through holes in substrate 114. A backing plate 150 is placed against one side of grommet matrix 116 so as to keep grommets 126 positioned within the holes in substrate 114. Grommets 126 may extend through the holes as depicted in FIG. 8. Dental tools, such as a shaft of a dental bur, may be placed in a hole 128 of a grommet 126. Holes 152 in backing plate 150 allow a shaft of the dental bur to extend therethrough into a space that is created by standoffs 154 that position backing plate 150 above the bottom of lower portion 118 within housing 112. This arrangement also holds substrate 114 at an elevated position relative to the bottom of lower portion 118 and sandwiches grommet matrix 126 between backing plate 150 and substrate 114. In this embodiment, grommets 126 have a substantially cylindrical outer surface and are interconnected by way of links 156. Links 156 may be substantially cylindrical having two ends, each of which are respectively attached to adjacent grommets 126. Each grommet 126 has at least two links 156 attached thereto, which serve to position grommets 126 in grommet matrix 116. Links 156 may have different thicknesses or diameters, which serve to position substrate 114 a predetermined distance from backing plate 150 and allows a sterilizing fluid or gas to flow around grommets 126 and links 156. If viewed in profile or in cross-section a grommet 126 and two links 156 connected thereto on opposite sides of grommet 126 will have a T-shaped look.

Additional features, such as instrument holding protrusions 158 may be connected to grommet matrix 116 and extend substantially through substrate 114. Protrusions 158 include features that serve to hold other surgical instruments, such as a dental pick.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dental case, comprising:
   a substrate having a plurality of holes therein;
   a grommet matrix including a plurality of grommets each having a groove, said plurality of grommets being interconnected outside of said groove, said plurality of grommets being located at predetermined positions corresponding to said plurality of holes;
   a membrane by which said plurality of grommets are interconnected, said membrane being configured to remain attached to said plurality of grommets at least until being removed subsequent to said plurality of grommets being installed in said substrate at said predetermined positions; and
   a weakened linkage between said membrane and each of said plurality of grommets, said membrane being made of the same material as said plurality of grommets, said membrane and said plurality of grommets being formed in the same molding operation, said membrane and said plurality of grommets being integral when formed.

2. The dental case of claim 1, wherein each of said plurality of grommets are positioned in a corresponding one of said plurality of holes, with a portion of said substrate substantially filling each of said grooves.

3. The dental case of claim 2, wherein said plurality of grommets are interconnected only by way of said substrate.

4. The dental case of claim 1, further comprising a housing in which said substrate is positioned.

5. A grommet assembly, comprising:
   a plurality of grommets each having a groove, said plurality of grommets being interconnected outside of said groove, said plurality of grommets being located at predetermined positions;
   a membrane by which said plurality of grommets are interconnected, said membrane being configured to remain attached to said plurality of grommets at least until being removed subsequent to said plurality of grommets being installed at said predetermined positions; and
   a weakened linkage between said membrane and each of said plurality of grommets, said membrane being made of the same material as said plurality of grommets, said membrane and said plurality of grommets being molded at the same time, said membrane and said plurality of grommets being integral when formed.

6. The assembly of claim 5, further comprising a substrate having a plurality of holes therein, each of said holes associated with a corresponding one of said plurality of grommets.

7. The assembly of claim 5, wherein each of said plurality of grommets are positioned in a corresponding one of said plurality of holes, with portions of said substrate substantially filling each said groove of said plurality of grommets.

8. The assembly of claim 7, wherein said plurality of grommets being interconnected only by way of said substrate.

9. The dental case of claim 1, wherein said membrane is not removed from said plurality of grommets.

10. The dental case of claim 1, wherein said plurality of grommets are positioned in said substrate and are interconnected only by way of said substrate.

* * * * *